United States Patent
Pruter

(10) Patent No.: US 7,850,664 B1
(45) Date of Patent: Dec. 14, 2010

(54) METHOD AND SYSTEM FOR PROTECTING AND USING BIOPSY SYSTEM INSTRUMENTS

(76) Inventor: Rick L. Pruter, 21 Woodcrest La. NE., Iowa City, IA (US) 52240

( * ) Notice: Subject to any disclaimer, the term of this patent is extended or adjusted under 35 U.S.C. 154(b) by 1287 days.

(21) Appl. No.: 10/906,673

(22) Filed: Mar. 1, 2005

(51) Int. Cl.
*A61M 5/00* (2006.01)
*A61M 5/32* (2006.01)
*A61B 10/00* (2006.01)

(52) U.S. Cl. .................. 604/263; 604/192; 600/562
(58) Field of Classification Search ............... 604/192, 604/263; 600/263, 562
See application file for complete search history.

(56) References Cited

U.S. PATENT DOCUMENTS

| | | | |
|---|---|---|---|
| 4,316,463 A * | 2/1982 | Schmitz et al. ............. 604/135 |
| 4,522,196 A | 6/1985 | Cunningham et al. |
| 4,695,274 A * | 9/1987 | Fox ............................ 604/198 |
| 4,782,841 A * | 11/1988 | Lopez ......................... 600/577 |
| 4,850,994 A * | 7/1989 | Zerbst et al. ................ 604/198 |
| 4,867,172 A * | 9/1989 | Haber et al. ................ 600/576 |
| 4,892,521 A * | 1/1990 | Laico et al. ................. 604/192 |
| 4,936,830 A * | 6/1990 | Verlier ........................ 604/110 |
| 5,015,240 A * | 5/1991 | Soproni et al. .............. 604/192 |
| 5,061,246 A | 10/1991 | Anapliotis |
| 5,078,483 A | 1/1992 | Herzberg |
| 5,168,863 A | 12/1992 | Kurtzer |
| 5,250,031 A * | 10/1993 | Kaplan et al. ............... 604/110 |
| 5,295,972 A * | 3/1994 | Mischenko ................. 604/192 |
| 5,336,187 A * | 8/1994 | Terry et al. ................. 604/110 |
| 5,348,544 A * | 9/1994 | Sweeney et al. ............. 604/192 |
| 5,433,221 A | 7/1995 | Adair |
| 5,469,863 A | 11/1995 | Shah |
| 5,490,524 A | 2/1996 | Williams et al. |
| 5,549,570 A * | 8/1996 | Rogalsky .................... 604/198 |
| 5,702,344 A * | 12/1997 | Silverstein .................. 600/104 |
| 5,707,362 A * | 1/1998 | Yoon ...................... 604/164.03 |
| 5,910,113 A | 6/1999 | Pruter |
| 5,925,020 A * | 7/1999 | Nestell ....................... 604/198 |
| 5,951,525 A * | 9/1999 | Thorne et al. ............... 604/198 |
| 5,980,488 A * | 11/1999 | Thorne ....................... 604/110 |
| 6,000,400 A | 12/1999 | Navis |
| 6,167,884 B1 | 1/2001 | Navis |
| 6,592,556 B1 * | 7/2003 | Thorne ....................... 604/192 |
| 6,860,871 B2 * | 3/2005 | Kuracina et al. ............ 604/192 |
| 6,949,086 B2 * | 9/2005 | Ferguson et al. ............ 604/198 |
| 7,087,024 B1 * | 8/2006 | Pruter ......................... 600/461 |
| 7,211,069 B2 * | 5/2007 | Lehmann .................... 604/198 |
| 7,300,423 B2 * | 11/2007 | Cocker et al. ............... 604/263 |
| 7,320,682 B2 * | 1/2008 | Cocker et al. ............... 604/198 |
| 7,361,159 B2 * | 4/2008 | Fiser et al. .................. 604/192 |
| 2002/0091360 A1 * | 7/2002 | Peters, III ................... 604/198 |
| 2004/0044318 A1 * | 3/2004 | Fiser et al. .................. 604/263 |
| 2005/0059936 A1 * | 3/2005 | Fiser et al. .................. 604/263 |
| 2008/0051715 A1 * | 2/2008 | Young et al. ................ 604/135 |
| 2008/0097312 A1 * | 4/2008 | Wilmot et al. .............. 604/117 |
| 2009/0270804 A1 * | 10/2009 | Mesa et al. .................. 604/111 |

* cited by examiner

*Primary Examiner*—Max Hindenburg
*Assistant Examiner*—Sean P Dougherty
(74) *Attorney, Agent, or Firm*—Simmons Perrine Moyer Bergman PLC

(57) ABSTRACT

A system and method for reducing the risk of contamination of a sterile biopsy system via using a sterile sheath with an exterior structure to aid in opening the sheath, and further having a self-sealing target disposed at an opposing closed end of said sheath.

17 Claims, 4 Drawing Sheets

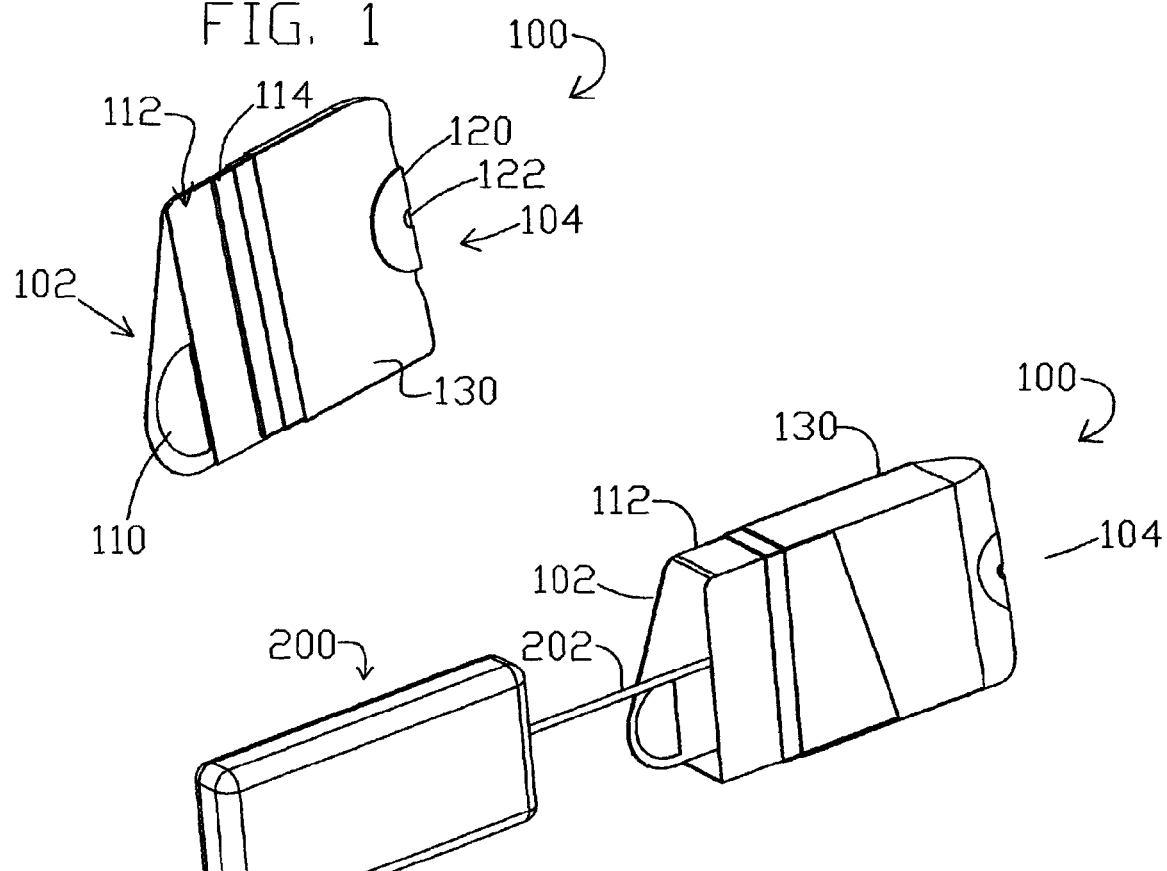
FIG. 1
FIG. 2
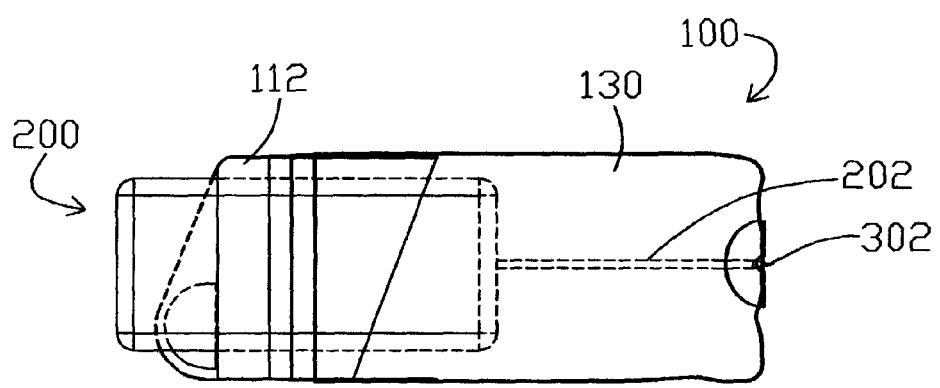
FIG. 3

METHOD AND SYSTEM FOR PROTECTING AND USING BIOPSY SYSTEM INSTRUMENTS

FIELD OF THE INVENTION

The present invention generally relates to medical equipment, and more particularly relates to medical equipment which must be covered with a sheath during medical procedures, and more particularly relates to methods and systems for permitting easy deployment of a sterile sheath over a biopsy system and for permitting insertion of a needle through said sheath while maintaining the sterile or aseptic state of the object inside the sheath.

BACKGROUND OF THE INVENTION

In recent years, medical professionals have used various types of biopsy systems to collect tissue from internal regions of the body. These biopsy systems are typically either enclosed in a sterile disposable sheath prior to use on any patient, or they are cleaned periodically. The biopsy system may be a mechanical or electro-mechanical device. Examples of a biopsy system are Vacora brand of biopsy system and Magnum made by CR Bard Company Aria by US Biopsy and Mammotone by Johnson Johnson. This is a vacuum-assisted breast biopsy system which is completely handheld. The biopsy needle is a sterile one-use item. Often, it is difficult to insert the biopsy system and the biopsy needle into a sheath. One example of a prior art sheath is disclosed in U.S. Pat. No. 5,910,113 to Rick L. Pruter, which shows a sheath with a support structure disposed inside the sheath at the open end (the opposite end is closed). Another example of a prior art sheath is disclosed in U.S. Pat. No. 5,061,246 to Emmanuel Anapliotis, which also has support structure at the open insertion end (this sheath also has an open opposing end).

While such sheaths have been used extensively in the past, the production of these sheaths is time consuming and, therefore, costly. They also provide limited protection in the case of the open-end design of Anapliotis and are susceptible to tears with the Pruter design if a needle or other instrument penetrates through the sheath.

Consequently, there exists a need for improved methods and systems for protecting biopsy systems in an efficient manner, while simultaneously maintaining the sterile or aseptic state of the system after a needle or other instrument pierces the sheath and travels from inside the sheath to outside the sheath.

SUMMARY OF THE INVENTION

It is an object of the present invention to provide a system and method for covering biopsy system equipment in an efficient manner.

It is a feature of the present invention to utilize a sterile sheath with an external structural support at the open end to aid in insertion of the biopsy system and other matter which may be disposed inside the sheath.

It is another feature of the present invention to include a sterile target coupled to the sterile sheath.

It is an advantage of the present invention to achieve improved efficiency in manufacturing sterile sheaths with an entry opening support structure.

It is an advantage of the present invention to provide reduced ability for tearing of a sterile sheath when a needle passes through the closed end.

It is another advantage of the present invention to reduce the opportunity for contamination of the biopsy system through the hole made by the needle.

The present invention is an apparatus and method for covering biopsy systems designed to satisfy the aforementioned needs, provide the previously stated objects, include the above-listed features, and achieve the already articulated advantages. The present invention is carried out in a "wasted time-less" manner in a sense that the time consumed during manufacturing with sealing an opening support structure within the sheath, has been eliminated. The invention is also accomplished in a "tear-less" or "contamination-less" manner in the sense that the contamination that may be exposed to the internal biopsy system through a tear in the sheath after a needle is caused to exit the inside of the sheath, has been reduced.

Accordingly, the present invention is a system and method including a sterile sheath disposed over a biopsy system with an external sheath entry end aiding structure, as well as a self-sealing target disposed at an opposite end.

BRIEF DESCRIPTION OF THE DRAWINGS

The invention may be more fully understood by reading the following description of the preferred embodiments of the invention, in conjunction with the appended drawings wherein:

FIG. 1 is a side view of the sheath system of the present invention, in a collapsed configuration before insertion of a biopsy system.

FIG. 2 is a perspective view of the external support structure sheath of FIG. 1 in conjunction with a representative biopsy system and needle during the process of insertion of the biopsy system into the sheath.

FIG. 3 is a side view of a sheath of FIG. 2 after the biopsy system has been inserted further into the sheath; the dotted lines reveal the view of the biopsy system and needle which are inside the sheath.

DETAILED DESCRIPTION

Figure 4:
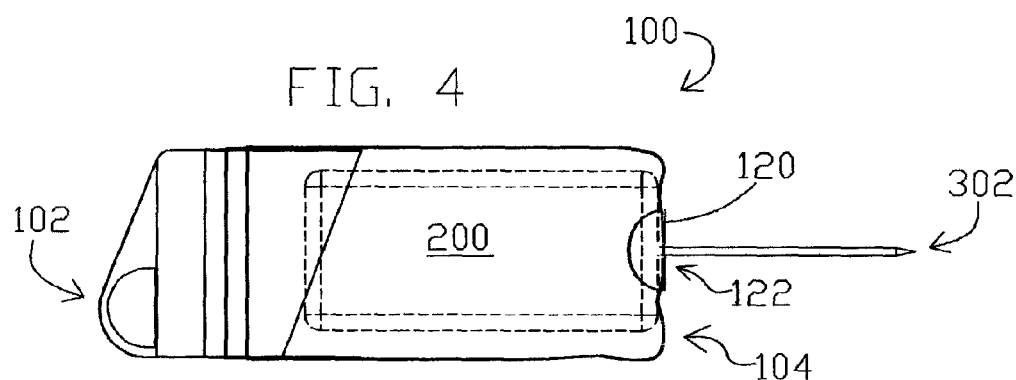
FIG. 4 is a side view of the sheath of FIG. 3 after the biopsy system and needle have been fully inserted; the dotted lines reveal the view of the biopsy system and needle which are inside the sheath.

Now referring to the drawings wherein like numerals refer to like matter throughout, and more specifically referring to FIG. 1, there is shown a biopsy system sheath system of the present invention generally designated 100, including a sheath body portion 130 having a biopsy system insertion end 102 and an opposing needle or cannula exiting end 104. Preferably, sheath body portion 130 is made of plastic film, similar to materials used in the prior art for sterile drapes and transceiver covers. In one embodiment, exterior sheath support structure top end 112 is made of a semi-rigid tape, having an adhesive on one side and a non-adhesive opposing side. Exterior sheath support structure top end 112 could also be a cardboard-like material with adhesive or a plastic-type material which can be "welded", using known techniques, to the sheath body portion 130. Exterior sheath support structure top end 112 can be disposed outside of the sheath body portion 130 by folding over an end section of the sheath body portion 130 so as to cover the exterior sheath support structure top end 112. A weld or other closure technique can be used to seal the exterior sheath support structure top end 112 within the new pouch created on the outside of the sheath body portion 130. Preferably, handle 110 and exterior sheath support structure top end 112 are detachably coupled to the sheath body portion 130 via a handle detaching perforation 114. Other means of easily removing the handle and top end 112 could be used as well. It should be understood that the present invention can be constructed with or without a handle 110. The sheath can be constructed so that the entire handle portion is removable after insertion of the biopsy system. This will permit the sheath to be closed by use of double-sided tape, Ziploc baggy-type seals or other ways to seal the open end. In this configuration, a perforation of the sheath between the exterior sheath support structure top end 112 and the sealing tape or baggy seal would facilitate complete detachment of the handle before the sheath is sealed up prior to use.

Preferably, the sheath body portion 130 is serially folded or folded like an accordion or otherwise configured to be automatically or telescopically deployed from a collapsed position to an expanded position with relative ease. Needle or cannula-receiving target 120 is preferably disposed at the needle or cannula-exiting end 104 at a central location; however, other orientations and locations of needle or cannula-receiving target 120 could be located elsewhere. In a preferred embodiment of the present invention, needle or cannula-receiving target 120 comprises a circular target having a semi-rigid characteristic and having a needle or cannula-exiting hole 122, which exposes a portion of the sheath. The relatively small hole surrounded by the target helps to limit tearing of the sheath after it is pierced by the needle. Needle or cannula-receiving target 120 may be made of tape or other material which is adhered to the exterior of sheath body portion 130. However, needle or cannula-receiving target 120 may be welded to sheath body portion 130. It may be disposed inside the sheath body portion 130 as well. This novel idea is capable of providing many benefits irrespective of minor deviations from the described preferred embodiment and preferred use. Needle or cannula-receiving target 120 may be colored or otherwise configured to provide for easy registration of the needle 202 with the needle or cannula-exiting hole 122. Needle or cannula-receiving target 120 may be made from the same material as exterior sheath support structure top end 112, and it may share the same or similar attachment means to the sheath body portion 130. Needle or cannula-receiving target 120 helps to prevent tearing of the sheath by adhering to the sheath in an area around the hole created by the needle, which area helps to absorb or spread out the forces on the sheath, which otherwise may result in tearing of the sheath beyond the piercing of the sheath by the needle or cannula. When the term "target" is used herein, it is intended to refer to any visible structure disposed interior or exterior to the sheath which is configured to aid in locating a point to pierce with the needle and simultaneously inhibit tearing of said sheath beyond the target when a needle or cannula pierces said sheath at said target. Needle or cannula-receiving target 120 may be as simple as a disk or other shaped adhesive patch-like object adhered to the sheath. In a more sophisticated design, needle or cannula-receiving target 120 could be an "O" ring or other flexible material, such as memory foam, or other material capable of receiving therethrough a needle or cannula and capable of returning to its original shape or near original shape upon removal of said needle or cannula.

A more detailed understanding of the present invention can be achieved by now referring to FIG. 2, which shows an enlarged perspective view of the sheath system 100 of FIG. 1. FIG. 2 further shows a biopsy system 200, which may be an ultrasound transducer or a gamma ray receiver or similar substitute. Exterior sheath support structure top end 112 is shown in a fully deployed orientation where it has been opened to form a hole or tunnel through which the needle 202 can be inserted. Exterior sheath support structure top end 112 is shown as being generally rectangular in shape so as to form a top-less and bottom-less rectangular box, through which the needle 202 and the biopsy system 200 are inserted. However, it should be understood that other non-rectangular shapes could be used as well.

An even more detailed understanding of the present invention may be achieved by now referring to FIG. 3, which shows the sterile sheath 100 with the needle 202 and biopsy system 200 partially disposed therein. The dashed lines show the biopsy system 200 and the needle 202 which would otherwise be concealed by the exterior sheath support structure top end 112, sheath body portion 130 and needle or cannula-receiving target 120. A portion of the handle 110 is shown in dashed lines as it is occluded from view by the biopsy system 200. Needle tip 302 is shown exiting from the needle or cannula-receiving target 120 through needle or cannula-exiting hole 122.

Now referring to FIG. 4, there is shown a system of the present invention after the biopsy system 200 has been fully inserted. The dotted lines show the biopsy system 200 hidden behind the sheath body portion 130.

Figure 5:
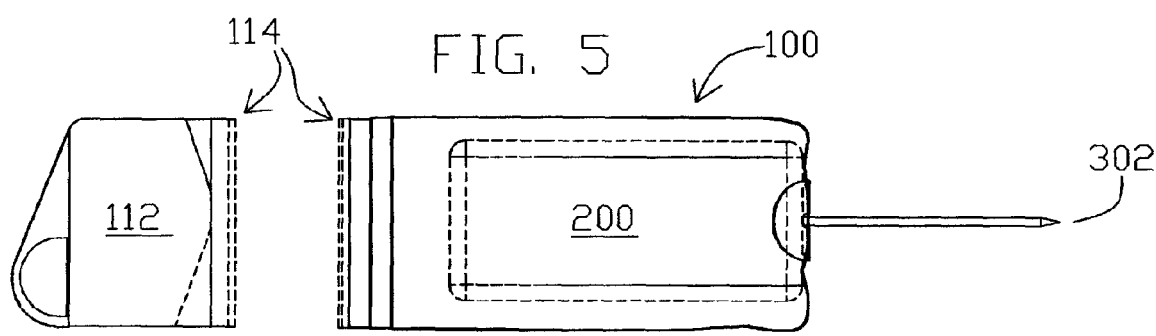
FIG. 5 is a side view of the sheath of FIG. 4 after the removable external structure and handle have been detached.

Now referring to FIG. 5, there is shown a system of the present invention after exterior sheath support structure top end 112 has been separated along handle detaching perforation 114.

Figure 6:
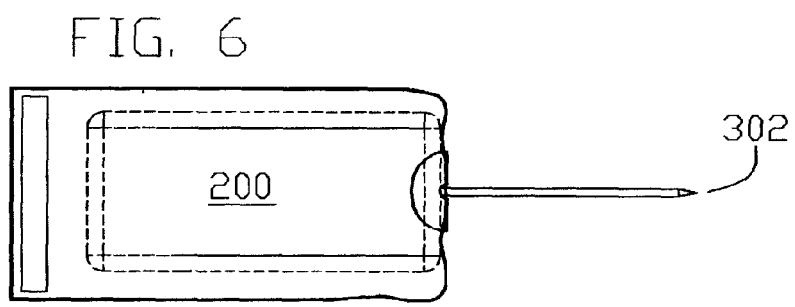
FIG. 6 is a side view of the sheath of FIG. 5 after the flap has been closed.

Now referring to FIG. 6, there is shown a system of FIG. 5 after the biopsy system insertion end 102 has been closed up. The biopsy system insertion end 102 is closed up by detaching the top end 112 along the perforation 114, and then it is folded over or rolled to seal off the end, and it is then held in place by an adhesive.

Figure 7:
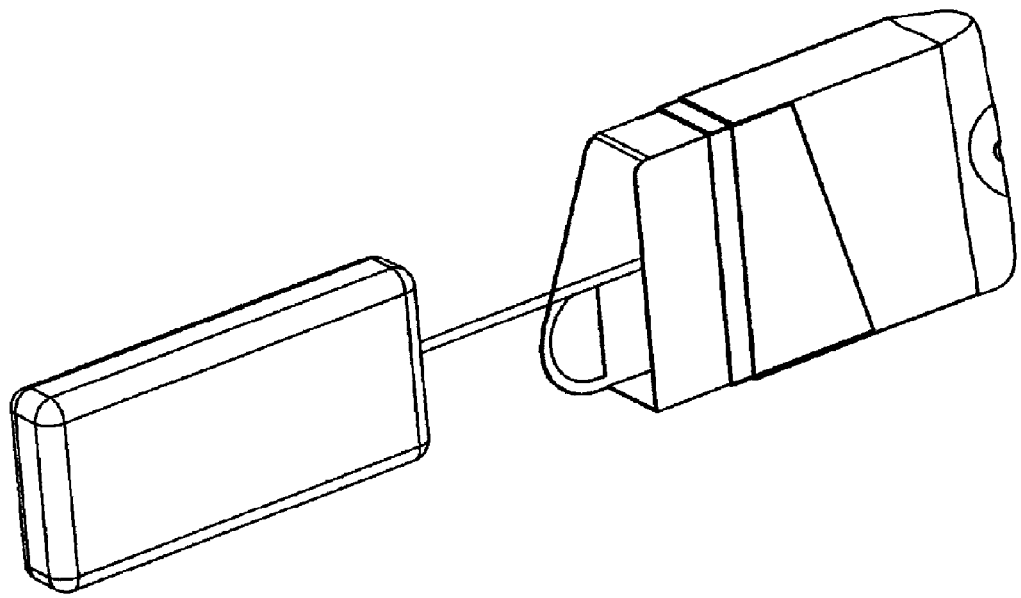
FIG. 7 is a perspective view of the sheath of FIG. 4 where the sheath is shown as transparent and the target is shown pierced at a central point by the needle.
Figure 7:
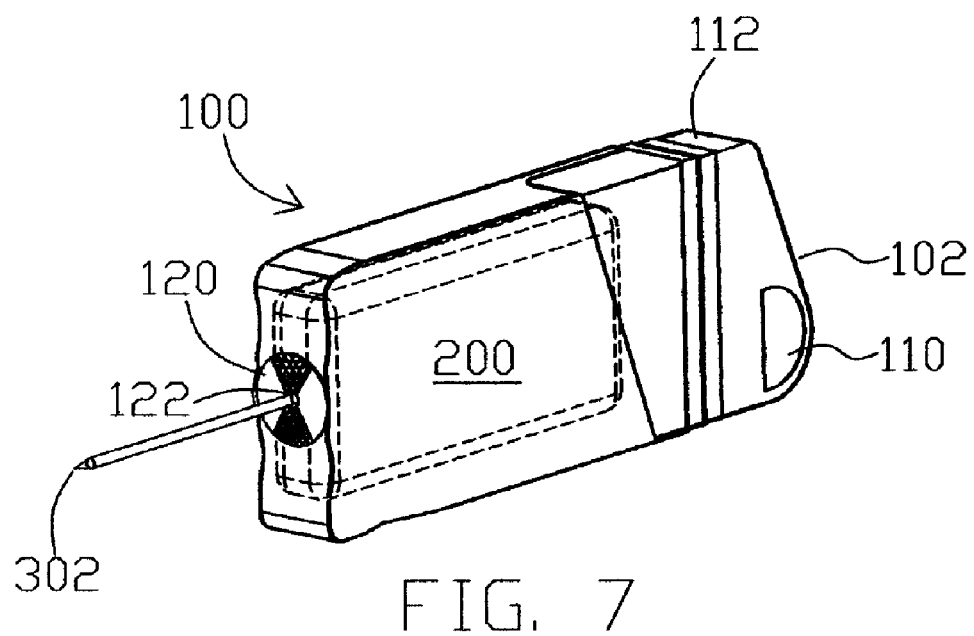

Now referring to FIG. 7, there is a perspective view of the system of the present invention.

Figure 8:
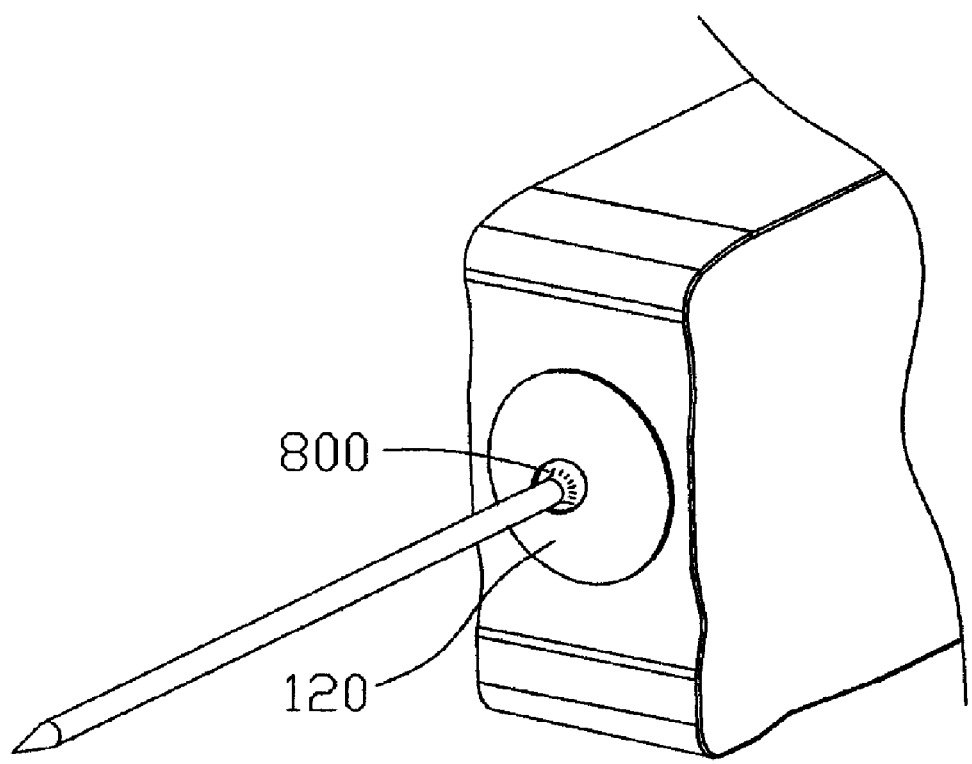
FIG. 8 is a perspective view of the needle or cannula-receiving target which shows that it has a needle or cannula exiting hole therein, as well as a concentric exterior backflow retarding seal.

Now referring to FIG. 8, there is shown a close-up perspective view of the needle or cannula-receiving target 120 with the needle or cannula-exiting hole 122. It is also shown to have a backflow retarding seal 800, which is designed to cling to the needle as it passes therethrough. The materials for the backflow retarding seal 800 may be plastic film or any suitable material which would tend to resist tearing while tending to cling to or be biased toward the needle. This clinging to or pressure on the needle helps to retard backward contamination of the biopsy system 200 through the needle or cannula-receiving target 120. It should be understood that the present invention can be utilized with or without the backflow retarding seal 800.

Figure 9:
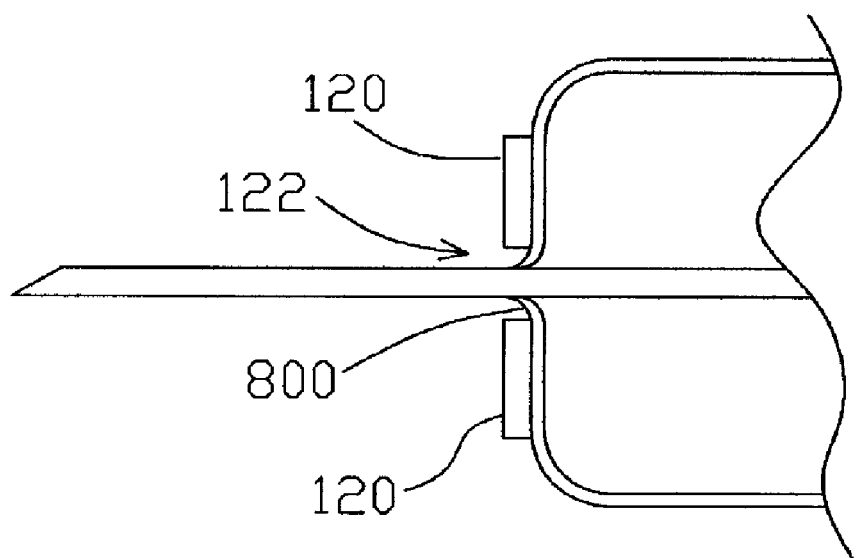
FIG. 9 is a cross-sectional view of the view of FIG. 8 which shows the sheath clinging to the needle and acting as a backflow retarding seal.

Now referring to FIG. 9, there is shown a cross-sectional view of the present invention as shown in FIG. 8. The backflow retarding seal 122 is shown as being made of the sheath itself. The sheath tends to cling to the needle, thereby demonstrating a backflow retarding characteristic. Other types of backflow retarding seals could be used as well.

In operation, the apparatus and method of the present invention as described in FIGS. 1-9, could function as follows: a biopsy system 200 with a needle 202 attached thereto is inserted by a physician into an opened biopsy system insertion end 102. The needle tip 302 of needle 202 pierces through the needle or cannula-exiting hole 122 of the needle or cannula-receiving target 120; the biopsy system 200 is further inserted until completely in the sheath body portion 130. The exterior sheath support structure top end 112 is then detached along handle detaching perforation 114, so that the sheath body portion 130 is not a hindrance during use of the biopsy system 200.

Throughout this description, reference is made to "sterile" or a "sterile sheath" or other "sterile items". It should be understood that this could refer to any state of cleanliness with respect to living organisms or a media upon which living organisms could grow. The present invention is intended to cover items that are aseptic, as well as sterile.

Throughout this description, reference is made to a physician. The present invention is intended to apply to any person, such as, but not limited to, physicians, physicians' assistants, nurses, medical imaging specialists, veterinarians, veterinarians' assistants, industrial clean room technicians, etc.

Throughout this description, reference is made to a biopsy system or other medical equipment. The present invention is intended to apply to any environment, such as, but not limited to, medical, veterinary or clean room applications, etc.

The term "outside the sheath" is used herein to mean being on a side of said sheath which is opposite a side of the sheath which is generally the inside of said sheath. This "outside of the sheath" is also meant to include within a pouch formed on the outside of the sheath by folding the outside of the sheath over onto itself.

The present invention is described in a preferred embodiment as having both an external-to-the-sheath support structure and a needle-receiving target. It should be understood that the target of the present invention can be used with an internal support structure, or it can be used with a sheath without any support structure. The external-to-the-sheath support structure of the present invention could likewise be used without either an internal or external needle target.

It is thought that the method and apparatus of the present invention will be understood from the foregoing description and that it will be apparent that various changes may be made in the form, construct steps, and arrangement of the parts and steps thereof, without departing from the spirit and scope of the invention or sacrificing all of their material advantages. The form herein described is merely a preferred exemplary embodiment thereof.

What is claimed is:

1. An apparatus for covering a biopsy system, the apparatus comprising:
   a self-expanding sheath having an open end and an opposing completely closed end;
   said self-expanding sheath sized and configured for receiving therein said biopsy system;
   a support structure disposed at said open end for aiding in insertion of a biopsy system into the self-expanding sheath;
   a penetration target disposed at said opposing completely closed end, said penetration target being configured to allow penetration therethrough by a needle and further configured to form a backflow retarding seal;
   said biopsy system comprising a hollow elongated sharp object; and
   said support structure disposed at said open end of said self-expanding sheath, said support structure being configured for holding open said open end.

2. The apparatus of claim 1 wherein said support structure is flexible.

3. The apparatus of claim 2 further comprising an adhesive, located to couple said support structure with said self-expanding sheath.

4. The apparatus of claim 2 wherein said support structure is disposed in a pouch formed by folding said self-expanding sheath.

5. The apparatus of claim 1 wherein said penetration target is disposed outside of said self-expanding sheath.

6. An apparatus for covering a biopsy system, the apparatus comprising:
   a self-expanding sterilizable sheath having an open end and an opposing completely closed end;
   said self-expanding sterilizable sheath sized and configured for receiving therein said biopsy system;
   a support structure disposed at said open end for aiding in insertion of a biopsy system into the self-expanding sterilizable sheath;
   a penetration target disposed at said opposing completely closed end;
   said biopsy system comprising an electronic imaging transceiver configured to transmit and receive signals out through and back in through said self-expanding sterilizable sheath;
   said support structure disposed outside said self-expanding sterilizable sheath and at said open end of said self-expanding sterilizable sheath, said support structure being configured for holding open said open end;
   wherein said penetration target is disposed outside of said self-expanding sterilizable sheath; and
   wherein said penetration target is coupled to said self-expanding sterilizable sheath with a contact adhesive.

7. A system for protecting a biopsy system comprising:
   an electronic imaging transceiver of said biopsy system;
   means for covering said electronic imaging transceiver of said biopsy system;
   means, exterior to said means for covering, for holding open said means for covering to aid insertion of said electronic imaging transceiver; and
   means for limiting tearing resulting from a puncture at a predetermined location.

8. The system of claim 7 wherein said means for covering comprises a sheath.

9. The system of claim 8 wherein said means, exterior to said means for covering, for holding open said means for covering comprises a flexible member comprising a contact adhesive side for coupling with said sheath.

10. The system of claim 9 wherein said means for limiting tearing comprises an adhesive-backed patch adhering to said sheath.

11. The system of claim 10 wherein said sheath comprises a perforation configured to permit rapid detachment of said flexible member from a remaining portion of said sheath.

12. An apparatus for covering a biopsy system, the apparatus comprising:
   a self-expanding sterilizable sheath having an open end and an opposing closed end;
   said self-expanding sterilizable sheath sized and configured for receiving therein said biopsy system;
   a support structure disposed at said open end for aiding in insertion of a biopsy system into the self-expanding sterilizable sheath;
   a penetration target disposed at said opposing closed end;

said biopsy system comprising an electronic imaging transceiver configured to transmit and receive signals out through and back in through said self-expanding sterilizable sheath;

said support structure disposed outside said self-expanding sterilizable sheath and at said open end of said self-expanding sterilizable sheath, said support structure being configured for holding open said open end;

wherein said support structure is flexible;

an adhesive, located to couple said support structure with an exterior of said self-expanding sterilizable sheath;

wherein said penetration target is disposed outside of said self-expanding sterilizable sheath;

wherein said penetration target is coupled to said self-expanding sterilizable sheath with a contact adhesive;

wherein said penetration target further comprises a closed sealing structure configured for limiting an extent of tearing and contamination through tears in said self-expanding sterilizable sheath when a needle is passed therethrough; and wherein said support structure further comprises a detachable perforated handle end.

13. An apparatus for covering a biopsy system, the apparatus comprising:

a self-expanding sterile sheath having an open end and an opposing closed end;

said self-expanding sterile sheath sized and configured for receiving therein said biopsy system;

a support structure disposed at said open end for aiding in insertion of a biopsy system into the self-expanding sterile sheath;

a penetration target disposed at said opposing closed end;

said biopsy system comprising an electronic imaging transceiver configured to transmit and receive signals out through and back in through said self-expanding sterile sheath;

said support structure disposed outside said self-expanding sterile sheath and at said open end of said self-expanding sterile sheath, said support structure being configured for holding open said open end;

wherein said support structure is flexible;

an adhesive, located to couple said support structure with said self-expanding sterile sheath's exterior;

wherein said penetration target is disposed outside of said self-expanding sterile sheath;

wherein said penetration target is coupled to said self-expanding sterile sheath with a contact adhesive;

wherein said penetration target further comprises a closed sealing structure configured for limiting an extent of tearing and contamination through tears in said self-expanding sterile sheath when a needle is passed therethrough; and wherein said support structure further comprises a detachable perforated handle end.

14. An apparatus for covering a biopsy system, the apparatus comprising:

a sheath having an open end and an opposing closed end, said sheath being expandable along an axis extending from said open end to said closed end;

said sheath sized and configured for receiving therein a hollow elongated pointed member;

a support structure disposed at said open end for aiding in insertion of a member into the sheath;

a penetration target disposed at said opposing closed end, said penetration target being configured to allow penetration therethrough by said member and further configured to form a backflow retarding seal;

said support structure disposed at said open end of said sheath, said support structure being configured for holding open said open end;

wherein said support structure has a shape which is not rigidly fixed;

wherein said penetration target is coupled to said sheath with a contact adhesive;

wherein said penetration target further comprising a closed sealing structure configured for limiting an extent of tearing and contamination through tears in said sheath when said member is passed therethrough; and wherein at least one of said sheath and said support structure is configured for manual manipulation to facilitate separation of said support structure from said sheath.

15. The system of claim 14 wherein the sheath is a sterilizable self-expanding sheath of a plastic film material, said penetration target and said support structure are disposed on an exterior surface of said sheath and said member is a needle.

16. The system of claim 14 wherein said support structure is a piece of cardboard and said member is a portion of a biopsy system which includes a medical imaging transceiver.

17. The system of claim 15 wherein said support structure is separated from said sheath by manually tearing said sheath along a perforation therein.

* * * * *